United States Patent [19]

Kolling et al.

[11] 3,968,314
[45] July 6, 1976

[54] BENZOYLPHENYLISOTHIOUREAS
[75] Inventors: Heinrich Kolling, Haan; Arno Widdig, Blecher; Herbert Thomas; Hans Peter Schulz, both of Wuppertal, all of Germany
[73] Assignee: Bayer Aktiengesellschaft, Germany
[22] Filed: Jan. 14, 1974
[21] Appl. No.: 433,084

[30] Foreign Application Priority Data
Jan. 23, 1973 Germany............................ 2303048

[52] U.S. Cl............................. 260/470; 260/347.2; 260/465 D; 260/562 P; 424/300; 424/285
[51] Int. Cl.²............................................ C07C 157/14
[58] Field of Search.................. 260/470; 260/465 D

[56] References Cited
UNITED STATES PATENTS

| | | | |
|---|---|---|---|
| 3,711,504 | 1/1973 | Adams et al. | 260/470 |
| 3,766,243 | 10/1973 | Widdig et al. | 260/470 |
| 3,796,710 | 3/1974 | Barker et al. | 260/243 R |
| 3,843,715 | 10/1974 | Widdig et al. | 260/470 |

*Primary Examiner*—Lorraine A. Weinberger
*Assistant Examiner*—Michael Shippen

[57] ABSTRACT

Benzoylphenylisothioureas of the formula:

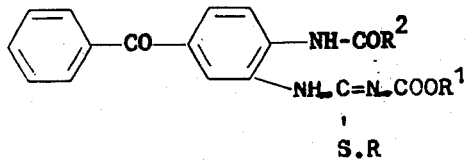

wherein
R is alkyl of 1 to 12 carbon atoms, cycloalkyl of 3 to 8 carbon atoms, alkenyl of 2 to 12 carbon atoms or aralkyl unsubstituted or substituted in the aryl moiety by one or more substituents selected from the group consisting of alkyl of 1 to 4 carbon atoms, alkoxy of 1 to 4 carbon atoms and halogen;
$R^1$ is alkyl of 1 to 4 carbon atoms, cyclohexyl or phenyl; and
$R^2$ is hydrogen; alkyl of 1 to 18 carbon atoms unsubstituted or substituted by one or more substituents selected from the group consisting of halogen, cyano, alkoxy of 1 to 4 carbon atoms, alkoxycarbonyl of 2 to 5 carbon atoms, phenoxy, halophenoxy, alkylphenoxy and alkoxyphenoxy; cycloalkyl of 5 to 8 carbon atoms; aralkyl unsubstituted or substituted in the aryl moiety by one or more substituents selected from the group consisting of halogen, alkyl of 1 to 4 carbon atoms and alkoxy of 1 to 4 carbon atoms; aryl unsubstituted or substituted by one or more substituents selected from the group consisting of halogen, alkyl of 1 to 4 carbon atoms and alkoxy of 1 to 4 carbon atoms; 1-furyl; or a moiety of the formula:

–NR″R‴ wherein
R″ is hydrogen or alkyl of 1 to 4 carbon atoms, and
R‴ is hydrogen; alkyl of 1 to 18 carbon atoms unsubstituted or substituted by one or more substituents selected from the group consisting of halogen, cyano, alkoxy of 1 to 4 carbon atoms and alkoxycarbonyl of 2 to 5 carbon atoms; cycloalkyl of 5 to 8 carbon atoms; aralkyl unsubstituted or substituted in the aryl moiety by one or more substituents selected from the group consisting of halogen, lower alkyl and lower alkoxy; phenyl unsubstituted or substituted by one or more substituents selected from the group consisting of halogen, lower alkyl and lower alkoxy; acyl of up to 18 carbon atoms unsubstituted or substituted by one or more substituents selected from the group consisting of halogen and lower alkoxy; aroyl unsubstituted or substituted by one or more substituents selected from the group consisting of halogen, lower alkyl and lower alkoxy; alkylsulphonyl of 1 to 18 carbon atoms unsubstituted or substituted by one or more substituents selected from the group consisting of halogen, amino, lower alkyl and lower alkoxy; or dialkylamino of 1 to 4 carbon atoms in each alkyl moiety; or
R″ and R‴ together with the nitrogen atom to which they are attached form a 4- to 7-membered heterocyclic ring wherein the nitrogen atom is the only heteroatom or wherein oxygen or sulfur is also present as a ring member,
are produced by reacting a thiourea of the formula:

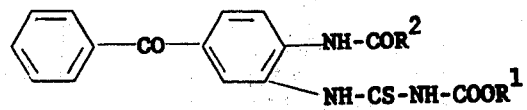

wherein
$R^1$ and $R^2$ are as above defined,
with an alkylating agent of the formula:

R — Y wherein
R is as above defined; and
Y is halogen, arylsulphonate or alkylsulphonate,
in the presence of a base and a diluent.

The benzoylphenylisothioureas described above are useful for their anthelmintic activity.

20 Claims, No Drawings

BENZOYLPHENYLISOTHIOUREAS

The present invention relates to benzoylphenylisothioureas, a process for their production, to anthelmintic compositions wherein said compounds are the active agents, and to methods of treating helmintic infections in humans and animals which comprises administering such benzoylphenylisothioureas.

Thiabendazole of the formula:

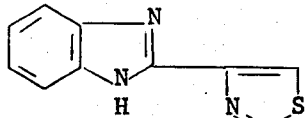

which is a known compound and is commercially available as an anthelmintic agent displays good anthelmintic activity. However, there is a need in the art for compounds which exhibit a substantially stronger action against helminths than thiabendazole.

It has now been discovered that benzoylphenylisothioureas of the formula:

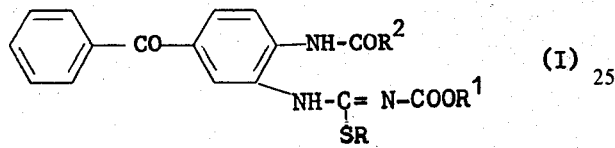

wherein
R is alkyl of 1 to 12 carbon atoms, cycloalkyl of 3 to 8 carbon atoms, alkenyl of 2 to 12 carbon atoms or aralkyl unsubstituted or substituted in the aryl moiety by one or more substituents selected from the group consisting of alkyl of 1 to 4 carbon atoms, alkoxy of 1 to 4 carbon atoms and halogen;

$R^1$ is alkyl of 1 to 4 carbon atoms, cyclohexyl or phenyl; and $R^2$ is hydrogen; alkyl of 1 to 18 carbon atoms unsubstituted or substituted by one or more substituents selected from the group consisting of halogen, cyano, alkoxy of 1 to 4 carbon atoms, alkoxycarbonyl of 2 to 5 carbon atoms, phenoxy, haophenoxy, alkylphenoxy and alkoxyphenoxy; cycloalkyl of 5 to 8 carbon atoms; aralkyl unsubstituted or substituted in the aryl moiety by one or more substituents selected from the group consisting of halogen, alkyl of 1 to 4 carbon atoms and alkoxy of 1 to 4 carbon atoms; aryl unsubstituted or substituted by one or more substituents selected from the group consisting of halogen, alkyl of 1 to 4 carbon atoms and alkoxy of 1 to 4 carbon atoms; 1-furyl; or a moiety of the formula:

-NR''R''' wherein
R'' is hydrogen or alkyl of 1 to 4 carbon atoms, and
R''' is hydrogen; alkyl of 1 to 18 carbon atoms unsubstituted or substituted by one or more substituents selected from the group consisting of halogen, cyano, alkoxy of 1 to 4 carbon atoms and alkoxycarbonyl of 2 to 5 carbon atoms; cycloalkyl of 5 to 8 carbon atoms; aralkyl unsubstituted or substituted in the aryl moiety by one or more substituents selected from the group cnsisting of halogen, lower alkyl and lower alkoxy; phenyl unsubstituted or substituted by one or more substituents selected from the group consisting of halogen, lower alkyl and lower alkoxy; acyl of up to 18 carbon atoms unsubstituted or substituted by one or more substituents selected from the group consisting of halogen and lower alkoxy; aroyl unsubstituted or substituted by one or more substituents selected from the group consisting of halogen, lower alkyl and lower akoxy; alkylsulphonyl of 1 to 18 carbon atoms unsubstituted or substituted by one or more substituents selected from the group consisting of halogen, amino, lower alkyl and lowr alkoxy; or dialkylamino of 1 to 4 carbon atoms in each alkyl moiety; or R'' and R''' together with the nitrogen atom to which they are attached from a 4- to 7-membered heterocyclic ring wherein the nitrogen atom is the only heteroatom or wherein oxygen or sulfur is also present as a ring member, exhibit stronger anthelmintic activity than thiabendazole.

The compounds of the present invention may be produced by reacting a thiourea of the formula:

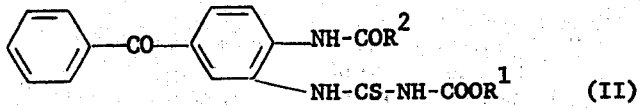

wherein
$R^1$ and $R^2$ are as above defined,
with an alkylating agent of the formula:

R — Y           (III)

wherein
is as above defined; and
Y is halogen, arylsulphonate, especially monoarylsulphonate, or alkylsulphate, especially lower alkylsulphate, in the presence of a base and a diluent.

As used herein, the term lower means moieties having from 1 to 6 carbon atoms.

If N-(2-acetamido-5-benzoylphenyl)-N'-methoxycarbonylthiourea methyl iodide and sodium hydroxide are used as starting materials, the course of the reaction in the process according to the invention can be represented by the following equation:

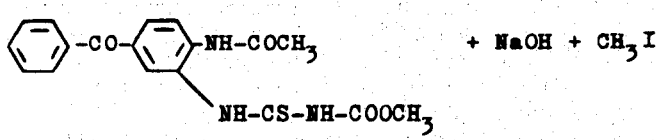

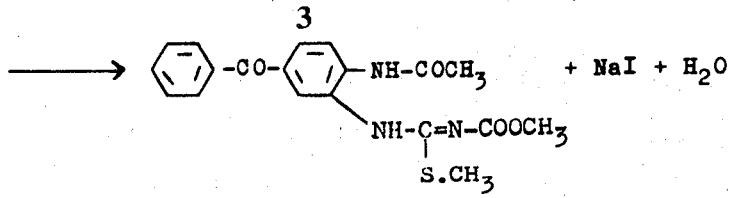 + NaI + H₂O

According to one embodiment of the present invention:

R is alkyl of 1 to 12 carbon atoms; cycloalkyl of 3 to 8 carbon atoms; alkenyl of 2 to 12 carbon atoms; or monaralkyl of 1 to 4 carbon atoms in the alkyl moiety unsubstituted or substituted in the aryl moiety by a member selected from the group consisting of alkyl of 1 to 4 carbon atoms, alkoxy of 1 to 4 carbon atoms and halogen;

$R^1$ is alkyl of 1 to 4 carbon atoms, cyclohexyl or phenyl; and $R^2$ is hydrogen; alkyl of 1 to 18 carbon atoms unsubstituted or substituted by a member selected from the group consisting of halogen, cyano, alkoxy of 1 to 4 carbon atoms, alkoxycarbonyl of 2 to 5 carbon atoms, phenoxy, halophenoxy, alkylphenoxy of 1 to 4 carbon atoms in the alkyl moiety, and alkoxyphenoxy of 1 to 4 carbon atoms in the alkoxy moiety; cycloalkyl of 5 to 8 carbon atoms; monoaralkyl of 1 to 4 carbon atoms in the alkyl moiety unsubstituted or substituted in the aryl moiety by a substituent selected from the group consisting of halogen, alkyl of 1 to 4 carbon atoms and alkoxy of 1 to 4 carbon atoms; monoaryl unsubstituted or substituted by a substituent selected from the group consisting of halogen, alkyl of 1 to 4 carbon atoms and alkoxy of 1 to 4 carbon atoms; -furyl; or a moiety of the formula:

$$-NR''R'''$$

wherein $R''$ is hydrogen or alkyl of 1 to 4 carbon atoms, and $R'''$ is hydrogen; alkyl of 1 to 18 carbon atoms unsubstituted or substituted by a substituent selected from the group consisting of halogen, cyano, alkoxy of 1 to 4 cabon atoms and alkoxycarbonyl of 2 to 5 carbon atoms; cycloalkyl of 5 to 8 carbon atoms; monoaralkyl of 1 to 4 carbon atoms in the alkyl moiety unsubstituted or substituted in the aryl moiety by a substituent selected from the group consisting of halogen, lower alkyl and lower alkoxy; phenyl unsubstituted or substituted by a substituent selected from the group consisting of halogen, lower alkyl and lower alkoxy; acyl of up to 18 carbon atoms unsubstituted or substituted by a substituent selected from the group consisting of halogen and lower alkoxy; monoaroyl unsubstituted or substituted by a substituent selected from the group consisting of halogen, lower alkyl and lower alkoxy; alkylsulphonyl of 1 to 18 carbon atoms unsubstituted or substituted by a substituent selected from the group consisting of halogen, amino, lower alkyl and lower alkoxy; or dialkylamino of 1 to 4 carbon atoms in each alkyl moiety; or $R''$ and $R'''$ together with the nitrogen atom to which they are attached form a 4- to 7-membered heterocyclic ring wherein the nitrogen atom is the only heteroatom or wherein oxygen or sulfur is also present as a ring member.

According to another embodiment of the present invention:

R is alkyl of 1 to 4 carbon atoms, alkenyl of 2 to 4 carbon atoms, cycloalkyl of 5 or 6 carbon atoms or benzyl;

$R^2$ is hydrogen; lower alkyl unsubstituted or substituted by a substituent selected from the group consisting of halogen and phenoxy; cycloalkyl of 5 or 6 carbon atoms; benzyl, phenyl unsubstituted or substituted by halogen or alkyl of 1 to 4 carbon atoms; 1-furyl; or a moiety of the formula:

$$-NR''R'''$$

wherein $R''$ is hydrogen or alkyl of 1 to 4 carbon atoms, and $R'''$ is hydrogen; lower alkyl unsubstituted or substituted by halogen, cyano or alkoxy of 1 to 4 carbon atoms; benzyl; or phenyl.

According to another embodiment of the present invention:

R is methyl, ethyl, isopropyl, allyl, cyclohexyl or benzyl;

$R^1$ is methyl, ethyl, isopropyl or sec.-butyl; and $R^2$ is methyl, ethyl, n-propyl, isopropyl, n-butyl, isobutyl, isoamyl, cyclopentyl, cyclohexyl, benzyl, phenoxymethyl, phenyl, p-tolyl, methylamino, propylamino, butylamino, ω-cyanopentylamino, 2-methoxyethylamino, 3-ethoxypropylamino, benzylamino or phenylamino.

According to another embodiment of the present invention:

R is alkyl of 1 to 4 carbon atoms, alkenyl of 2 to 4 carbon atoms, or cyclohexyl;

$R^1$ is alkyl of 1 to 4 carbon atoms; and $R^2$ is lower alkyl, cycloalkyl of 5 or 6 carbon atoms, phenyl, phenoxymethyl, benzyl, mono-lower alkylamino, cyano lower alkylamino, lower alkoxy lower alkylamino, benzylamino or phenylamino.

According to another embodiment of the present invention:

R is methyl, ethyl, isopropyl, allyl or cyclohexyl;

$R^1$ is methyl, ethyl, isopropyl or sec.-butyl; and $R^2$ is methyl, ethyl, propyl, isopropyl, butyl, isobutyl, amyl, isoamyl, cyclopentyl, cyclohexyl, phenyl, phenoxymethyl, benzyl, methylamino, ethylamino, butylamino, ω-cyanopentylamino, -methoxyethylamino benzylamino or phenylamino.

According to another embodiment of the present invention;

R is alkyl of 1 or 2 carbon atoms;

$R^1$ is alkyl of 1 or 2 carbon atoms, cyclohexyl or phenyl; and $R^2$ is hydrogen, alkyl of 1 to 4 carbon atoms, cyclohexyl or phenyl.

According to another embodiment of the present invention:

R is methyl;

$R^1$ is methyl, ethyl, cyclohexyl or phenyl; and $R^2$ is methyl, ethyl, propyl, cyclohexyl or phenyl.

Y is preferably halogen or lower alkylsulphate, especially iodine or methosulphate.

Representative alkylating agents which can be used in the process of the present invention include: methyl iodide, ethyl iodide, isopropyl iodide, cyclohexyl bromide, dimethyl sulphate, toluenesulphonic acid methyl ester, allyl bromide and benzyl chloride. These compounds are generally known per se.

The benzoylphenylthioureas of the formula (II) which are used as starting materials according to the process of the present invention are not per se known. However, they can be prepared in a manner analogous to the process as disclosed in the literature. Thus for example, one may obtain N-(2-acetamido-5-benzoylphenyl)-N'-methoxycarbonyl-thiourea from 2-nitro-4-benzoylaniline, described in the literature (see for example, Ber. Dtsch. Chem. Ges. 47, 2778), in a three-stage process as follows:

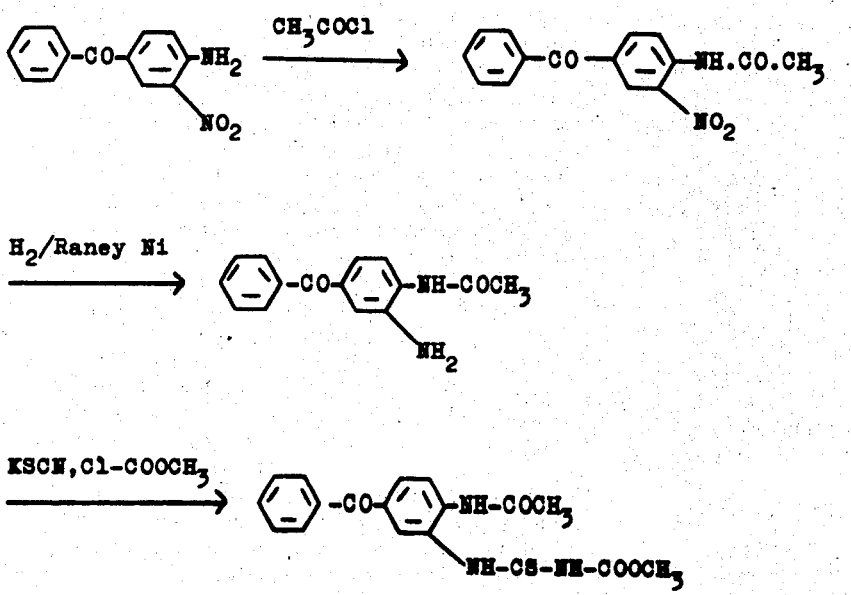

The following benzoylphenylthioureas are representative of those of the formula (II) used as starting materials according to the process of the present invention:

N-(2-acetaido-5-benzoylphenyl)-N'-methoxycarbonyl-thiourea,
N-(2-acetamido-5-benzoylphenyl)-N'-ethoxycarbonyl-thiourea,
N-(2-acetamido-5-benzoylphenyl)-N'-isopropoxycarbonyl-thiourea,
N-(2-acetamido-5-benzoylphenyl)-N'-sec.-butoxycarbonyl-thiourea,
N-(2-propionamido-5-benzoylphenyl)-N'-methoxycarbonyl-thiourea,
N-(2-butyramido-5-benzoylphenyl)-N'-methoxycarbonyl-thiourea,
N-(2-isobutyramido-5-benzoylphenyl)-N'-methoxycarbonyl-thiourea,
N-(2-valeramido-5-benzoylphenyl)-N'-methoxycarbonyl-thiourea,
N-(isovaleramido-5-benzoylphenyl)-N'-methoxycarbonyl-thiourea,
N-(2-capronamido-5-benzoylphenyl)-N'-methoxycarbonyl-thiourea,
N-(2-isocapronamido-5-benzoylphenyl)-N'-methoxycarbonyl-thiourea,
N-(2-cyclopentanecarbonamido-5-benzoylphenyl)-N'-methoxy-carbonyl-thiourea,
N-(2-cyclohexanecabonamido-5-benzoylphenyl)-N'-methoxy-carbonyl-thiourea,
N-(2-phenylacetamido-5-benzoylphenyl)-N'-methoxycarbonyl-thiourea,
N-(2-phenoxyacetamido-5-benzoylphenyl)-N'-methoxycarbonyl-thiourea,
N-(2-benzamido-5-benzoylphenyl)-N'-methoxycarbonyl-thiourea,
N-(2-(2'-methylureido)-5-benzoylphenyl)-N'-methoxycarbonyl-thiourea,
N-(2-(2'-ethylureido)-5-benzoylphenyl)-N'-methoxycarbonyl-thiourea,
N-(2-(2'-butylureido)-5-benzoylphenyl)-N'-methoxycarbonyl-thiourea,
N-(2-(2'-ω-cyanopentylureido)-5-benzoylphenyl)-N'-methoxy-carbonyl-thiourea,
N-(2-(2'-β-methoxyethylureido-5-benzoylphenyl)-N'-methoxy-carbonyl-thiourea, N-(2-(2'-benzylureido)-5-benzoylphenyl)-N'-methoxycarbonyl-thiourea, and
N-(2-(2'-phenylureido)-5-benzoylphenyl)-N'-methoxycarbonyl-thiourea, Diluents which are used according to the process of the present invention include water and organic solvents, such as alcohols, acetone, dimethylsulphoxide, dimethylformamide and acetonitrile, either by themselves or mixed with water.

The bases which can be used according to the process of the present invention include the normal basic substances known per se in the art. Preferably, however, potassium hydroxide, sodium hydroxide, sodium carbonate or sodium bicarbonate is used.

The reaction temperatures can be varied over a substantial range. Generally, however, the reaction is carried out at between −10°C and +40°C and particularly at between 0°C and +30°C.

In carrying out the process according to the present invention, 1 mol of alkylating agent and 1 mol of base are usually employed per 1 mol of amidobenzoyl-phenylthiourea of formula (II). Excess alkylating agent and base can be used without disadvantage. The products can be worked up by introducing the reaction mixture into water and filtering off the product precipitated, drying it and purifying it by recrystallization.

The following compounds are representative of the benzoylphenylisothioureas of the present invention:

N-(2-acetamido-5-benzoylphenyl)-N'-methoxycarbonyl-S-methylisothiourea,
N-(2-acetamido-5-benzoylphenyl)-N'-ethoxycarbonyl-S-methylisothiourea,
N-(2-acetamido-5-benzoylphenyl)-N'-isopropoxycarbonyl-S-methylisothiourea,
N-(2-acetamido-5-benzoylphenyl)-N'-sec.-butoxycarbonyl-S-methylisothiourea,
N-(2-propionamido-5-benzoylphenyl)-N'-methoxycarbonyl-S-methylisothiourea,
N-(2-butyramido-5-benzoylphenyl)-N'-methoxycarbonyl-S-methylisothiourea,
N-(2-isobutyramido-5-benzoylphenyl)-N'-methoxycarbonyl-S-methylisothiourea,
N-(2-valeramido-5-benzoylphenyl)-N'-methoxycarbonyl-S-methylisothiourea,
N-(2-isovaleramido-5-benzoylphenyl)-N'-methoxycarbonyl-S-methylisothiourea,
N-(2-capronamido-5-benzoylphenyl)-N'-methoxycarbonyl-S-methylisothiourea,
N-(2-isocapronamido-5-benzoylphenyl)-N'-methoxycarbonyl-S-methylisothiourea,
N-(2-cyclopentanecarbonamido-5-benzoylphenyl)-N'-methoxycarbonyl-S-methylisothiourea,
N-(2-cyclohexanecarbonamido-5-benzoylphenyl)-N'-methoxycarbonyl-S-methylisothiourea,
N-(2-phenylacetamido-5-benzoylphenyl)-N'-methoxycarbonyl-S-methylisothiourea,
N-(2-phenoxyacetamido-5-benzoylphenyl)-N'-methoxycarbonyl-S-methylisothiourea,
N-(2-benzamido-5-benzoylphenyl)-N'-methoxycarbonyl-S-methylisothiourea,
N-(2-(2'-methylureido)-5-benzoylphenyl)-N'-methoxycarbonyl-S-methylisothiourea,
N-(-(2'-ethylureido)-5-benzoylphenyl)-N'-methoxycarbonyl-S-methylisothiourea,
N-(2-(2'-butylureido)-5-benzoylphenyl)-N'-methoxycarbonyl-S-methylisothiourea,
N-(2-(2'ω-cyanopentylureido)-5-benzoylphenyl)-N'-methoxycarbonyl-S-methylisothiourea,
N-(2-(2'-β-methoxyethylureido)-5-benzoylphenyl)-N'-methoxycarbonyl-S-methylisothiourea,
N-(2-(2'-benzylureido)-5-benzoylphenyl)-N'-methoxycarbonyl-S-methylisothiourea, N-(2-(2'-phenylureido)-5-benzoylphenyl)-N'-methoxycarbonyl-S-methylisothiourea,
N-(2-acetamido-5-benzoylphenyl)-N'-methoxycarbonyl-S-ethylisothiourea,
N-(2-acetamido-5-benzoylphenyl)-N'-methoxycarbonyl-S-isopropylisothiourea,
N-(2-acetamido-5-benzoylphenyl)-N'-methoxycarbonyl-S-allylisothiourea,
N-(2-acetamido-5-benzoylphenyl)-N'-methoxycarbonyl-S-cyclohexylisothiourea, and
N-(2-acetamido-5-benzoylphenyl)-N'-methoxycarbonyl-S-benzylisothiourea, The anthelmintic activity of the compounds of the present invention is particularly exemplified by the high level of activity and broad action against a variety of nematodes and cestodes including the following:

1. Hookworms (for example *Bunostomum trigonocephalum* and *Uncinaria stenocephala*).
2. trichostrongylides (for example *Haemonchus contortus, Trichostronglyus colubriformis, Nippostrongylus muris Cooperia curticei*).
3. Stronglyides (for example *Oesophagostomum columbianum*).
4. Rhabditides (for example *Strongyloides ratti*).
5. Eelworms (for example *Toxocara canis, Toxascaris leonina* and *Ascaris suum*).
6. Threadworms (for example *Aspiculuris tetraptera*).
7. Heterakides (for example *Heterakis spumosa*).
8. Whipworms (for example *Trichuris muris*).
9. Filariae (for example *Litomosoides carinii* and *Dipetalonema witei*).
10. Cestodes (for example *Taenia pisiformis, Echinococcus multilocularis* and Moniezia sp.).

The anthelmintic activity of the compounds of the present invention has been demonstrated by oral administration of representative compounds of the present invention in test animals which have been heavily infected with parasites. The dosages administered were well tolerated by the test animals.

The present invention thus includes both pharmaceutical compositions intended for human administration as well as veterinary compositions intended for animal administration. The words "pharmaceutical composition" as used below are thus intended to broadly include both particular types of compositions.

The pharmaceutical compositions of the present invention contain a major or minor amount e.g. 99.5% to 0.1. %, preferably 95% to 0.5% of at least one benzoylphenylisothiourea as above defined in combination with a pharmaceutically acceptable non-toxic, inert diluent or carrier, the carrier comprising one or more solid, semi-solid or liquid diluent, filler and formulation adjuvant which is non-toxic, inert and pharmaceutically acceptable. Such pharmaceutical compositions are preferably in dosage unit form; i.e., physically discrete units containing a predetermined amount of the drug corresponding to a fraction or multiple of the dose which is calculated to produce the desired thereapeutic response. The dosage units can contain one, two, three, four or more single doses or, alternatively, one-half, third or fourth of a single dose. A single dose preferably contains an amount sufficient to produce the desired therapeutic effect upon administration at one application of one or more dosage units according to a predetermined dosage regimen, usually a whole, half, third or quarter of the daily dosage administered once, twice, 3 or 4 times a day. Other therapeutic agents can also be present.

Although the dosage and dosage regimen must in each case be carefully adjusted, utilizing sound professional judgement and considering the age, weight and condition of the recipient, the route of administration and the nature and gravity of the illness, generally the dosage will be from 1 mg to 100 mg/kg of ody weight per day. In some instances a sufficient thereapeutic effect can be obtained at a lower dose while in others, a larger dose will be required.

Oral administration can be effected utilizing solid and liquid dosage unit forms such as powders, tablets, dragees, capsules, granulates, suspensions, solutions and the like.

Powders are prepared by comminuting the compound to a suitable fine size and mixing with a similarly comminuted pharmaceutical carrier such as an edible carbohydrate as for example starch, lactose, sucrose, glucose or mannitol. Sweetening, flavoring, preservative, dispersing and coloring agents can also be present.

Capsules are made by preparing a powder mixture as described above and filling formed gelatin sheaths.

Glidants and lubricants such as colloidal silica, talc, magnesium stearate, calcium stearate or solid polyethylene glycol can be added to the powder mixture before the filling operation. A disintegrating or solubilizing agent such as agar-agar calcium carbonate or sodium carbonate can also be added to improve the availability of the medicament when the capsule is ingested.

Tablets are formulated for example by preparing a powder mixture, granulating or slugging, adding a lubricant and disintegrant and pressing into tablets. A powder mixture is prepared by mixing the compound, suitably comminuted, with a diluent or base as described above, and optionally with a binder such as carboxymethyl, cellulose, an alginate, gelatin, or polyvinyl pyrrolidone, a solution retardant such as paraffin, a resorption accelerator such as a quaternary salt and/or an absorption agent such as bentonite, kaolin or dicalcium phosphate. The powder mixture can be granulated by wetting with a binder such as syrup, starch paste, acacia mucilage or solutions of cellulosic or polymeric materials and forcing through a screen. As an alternative to granulating, the powder mixture can be run through the tablet machine and the resulting imperfectly formed slugs broken into granules. The granules can be lubricated to prevent sticking to the tablet forming dies by means of the addition of stearic acid, a stearate salt, talc or mineral oil. The lubricated mixture is then compressed into tablets. The medicaments can also be combined with free flowing inert carriers and compressed into tablets directly without going through the granulating or slugging steps. A clear or opaque protective coating consisting of a sealing coat of shellac, a coating of sugar or polymeric material and a polish coating of wax can be provided. Dyestuffs can be added to these coatings to distinguish different unit dosages.

Oral fluids such as solutions, syrups and elixirs can be prepared in dosage unit form so that a given quantity contains a predetermined amount of the compund. Syrups can be prepared by dissolving the compound in a suitably flavored aqueous sucrose solution while elixirs are prepared through the use of a non-toxic alcoholic vehicle. Suspensions can be formulated by dispersing the compound in a non-toxic vehicle. Solubilizers and emulsifiers such as ethoxylated isostearyl alcohols and polyoxyethylene sorbitol esters, preservatives flavor additives such as peppermint oil or saccharin, and the like can also be added.

Where appropriate, dosage unit formulations for oral administration can be microencapsulated. The formulation can also be prepared to prolong or sustain the release as for example by coating or embedding particulate material in polymers, wax or the like.

Parenteral administration can be effected utilizing liquid dosage unit forms such as sterile solutions and suspensions intended for subcutaneous, intramuscular or intravenous injection. These are prepared by suspending or dissolving a measured amount of the compound in a non-toxic liquid vehicle suitable for injection such as an aqueous or oleaginous medium and sterilizing the suspension or solution. Alternatively, a measured amount of the compound is placed in a vial and the vial and its contents are sterilized and sealed. An accompanying vial or vehicle can be provided for mixing prior to administration. Non-toxic salts and salt solutions can be added to render the injection isotonic. Stabilizers, preservatives and emulsifiers can also be added.

Rectal administration can be effected utilizing suppositories in which the compound is admixed with low melting water soluble or insoluble solids such as polyethylene glycol, cocoa butter, higher esters as for example myristyl palmitate, or mixtures thereof.

Topical administration can be effected utilizing solid dosage unit forms such as powders or liquid or semiliquid dosage unit forms such as solutions, suspensions, ointments, pastes, creams and gels. The powders are formulated utilizing such carriers as talc, bentonite, silicic acid, polyamide powder and the like. Liquid and semiliquid formulations can utilize such carriers, in addition to those described above, as polyethylene glycol, vegetable and mineral oils, alcohols such as isopropanol and the like. Other excipients such as emulsifiers, preservatives, colorants, perfumes and the like can also be present. Formulations can also be administered as an aerosol, utilizing the usual propellants such as the chlorofluorohydrocarbons.

The preferred daily dose is 50 mg to 10 g of active ingredient.

The routes of administration include, oral parenteral (especially subcutaneous), rectal or dermal, preferably oral.

The following Example A through H demonstrate the anthelmintic activity of compounds representative of those of the present invention and also show for comparison the activity of the prior art compound thiabendazole:

EXAMPLE A

Hookworm test/sheep

Sheep experimentally infected with *Bunostomum trigono cephalum* were treated at the end of the pre-patency time of the parasites. The amount of active compound was administered orally as pure active compound in gelatine capsules.

The degree of action was determined by counting the worms expelled after the treatment and the worms surviving in the test animals after dissection and calculating the percentage of worms expelled.

The active compounds tested, the dosages used and the action can be seen from Table 2 which follows. Table 1 gives the active compounds and the minimum dosage in mg of active compounds per kg of body weight of the test animal which reduces the worm infection of the test animals by more than 90%.

Hookworm test/dogs

Dogs experimentally infected with *Uncinaria stenocephala* were treated at the end of the pre-patency of the parasites.

The amount of active compound was administered orally as pure active compound in gelatine capsules.

The degree of action was determined by counting the worms expelled after the treatment and the worms remaining in the test animal after dissection and calculating the percentage of worms expelled.

The table which follows gives the active compounds, the type of parasite and the minimum dosage which reduces the worm infection of the test animals by more than 90% ("red. >90%") in comparison to commercially available preparations.

The dosage is given in mg of active substance per kg of body weight.

EXAMPLE B

Stomach and intestine worm test/sheep

Sheep experimentally infected with *Haemonchus contortus*, *Cooperia curticei* or *Trichostrongylus colubriformis* were treated at the end of the pre-patency time of the parasites.

The amount of active compound was administered orally as pure active compound in gelatine capsules.

The degree of action was determined by quantitatively counting the worm eggs excreted with the faeces before and after the treatment.

Complete stoppage of the excretion of eggs after the treatment means that the worms have been expelled or have been damaged to such a point that they can no longer produce any eggs (effective dose).

The results are given in Table 2.

Table 1

(accompanying Example A)

| Active compound according to the invention | Parasite | Minimum effective dose (red. >90%) in mg/kg |
|---|---|---|
| [Structure: Ph–CO–C₆H₃(NH-CO-CH₃)(NH-C(SCH₃)=N-COOCH₃)] | Bunostomum | 5 |
|  | Uncinaria | 3 × 1 |
| [Structure: Ph–CO–C₆H₃(NH-CO-cyclohexyl H)(NH-C(SCH₃)=N-COOCH₃)] | Bunostomum | 10 |
| [Structure: Ph–CO–C₆H₃(NH-CO-CH₂-CH₃)(NH-C(S-CH₃)=N-COOCH₃)] | Bunostomum | 10 |
| [Structure: Ph–CO–C₆H₃(NH-CO-CH₂-CH₂-CH₃)(NH-C(S-CH₃)=N-COOCH₃)] | Bunostomum | 10 |
| Known preparation for comparison | | |
| [Structure: benzimidazole-2-yl thiazole] | Bunostomum | 75 |
|  | Uncinaria | Partial action only |

Table 2

(accompanying Example B)

| Active compound according to the invention | Parasite | Minimum effective dose (red. >90%) in mg/kg |
|---|---|---|
| Ph-CO-C6H3(NH-CO-CH3)(NH-C(SCH3)=N-COOCH3) | Haemonchus | 10 |
| | Trichostrongylus | 5 |
| | Cooperia | 10 |
| Ph-CO-C6H3(NH-CO-CH2-CH2-CH3)(NH-C(SCH3)=N-COOCH3) | Haemonchus | 10 |
| | Trichonstrongylus | 5 |
| Ph-CO-C6H3(NH-CO-C6H11)(NH-C(SCH3)=N-COOCH3) | Haemonchus | 10 |
| | Trichostrongylus | 5 |
| Ph-CO-C6H3(NH-CO-CH2-CH3)(NH-C(SCH3)=N-COOCH3) | Haemonchus | 10 |
| | Trichostrongylus | 2,5 |
| Known preparation for comparison — benzimidazole-thiazole | Haemonchus | 50 |
| | Trichostrongylus | 25 |
| | Cooperia | 25 |

EXAMPLE C

Knotworm test/sheep

Sheep experimentally infected with *Oesophagostomum columbianum* were treated at the end of the pre-patency time of the parasites.

The active compound was administered orally as pure active compound in gelatine capsules.

The degree of action was determined by counting the worms expelled after the treatment and the worms remaining in the test animals after dissection and calculating the percentage of worms expelled.

The results are shown in Table 3.

Table 3

(accompanying Example C)

| Active compound according to the inventin | Minimum effective dose (red. >90%) in mg/kg |
|---|---|
| Ph-CO-C6H3(NH-CO-CH3)(NH-C(SCH3)=N-COOCH3) | 10 |

Table 3-continued
(accompanying Example C)

| Active compound according to the invention | Minimum effective dose (red. >90%) in mg/kg |
|---|---|
| [structure: phenyl-CO-phenyl-NH-CO-cyclohexyl(H); with NH-C(SCH₃)=N-COOCH₃] | 10 |
| [structure: phenyl-CO-phenyl-NH-CO-CH₂-CH₂-CH₃; with NH-C(S-CH₃)=N-COOCH₃] | 10 |
| [structure: phenyl-CO-phenyl-NH-CO-CH₂-CH₃; with NH-C(S-CH₃)=N-COOCH₃] | 10 |

Known preparation for comparison

| [benzimidazole-thiazoline structure] | 35 |

EXAMPLE D

*Strongyloides ratti/rat*

Rats experimentally infected with *Strongyloides ratti* were treated at the end of the pre-patency time of the parasites. The amount of active compound was administered orally as an aqueous suspension.

The degree of activity of the compound was determined by counting, after dissection, the worms remaining in the test animal in comparison to untreated control animals and calculating the percentage action therefrom.

The results are given in Table 4.

Table 4
(accompanying Example D)

| Active compound according to the invention | Minimum effective dose (red. >90%) in mg/kg |
|---|---|
| [structure: phenyl-CO-phenyl-NH-CO-CH₃; with NH-C(SCH₃)=N-COOCH₃] | 5 |
| [structure: phenyl-CO-phenyl-NH-CO-CH₂-CH₂-CH₃; with NH-C(SCH₃)=N-COOCH₃] | 5 |
| [structure: phenyl-CO-phenyl-NH-CO-cyclohexyl(H); with NH-C(SCH₃)=N-COOCH₃] | 10 |
| [structure: phenyl-CO-phenyl-NH-CO-phenyl; with NH-C(SCH₃)=N-COOCH₃] | 25 |
| [structure: phenyl-CO-phenyl-NH-CO-CH₂-CH₃; with NH-C(SCH₃)=N-COOCH₃] | 5 |

Known preparation for comparison

| [benzimidazole-thiazoline structure] | 25 |

EXAMPLE E

Eelworm test/dogs and rats

The amount of active compound was administered orally as pure active compound in gelatine capsule to dogs naturally or experimentally infected with *Toxascaria leonina* or *Toxocara canis*.

The degree of action was determined by counting the worms expelled after the treatment and the worms remaining in the test animals after dissection and calculating the percentage of the worms expelled.

Rats experimentally infected with *Ascaris suum* were treated 2 to 4 days after infection. The active compound was administered orally as an aqueous suspension.

The degree of action of the compound is determined by counting, after dissection, the worms remaining in the test animal in comparison to untreated control animals and calculating the percentage action therefrom.

The results are given in Table 5.

Table 5

(accompanying Example E)

| Active compound according to the invention | Parasite | Minimum effective dose (red. >90%) in mg/kg |
| --- | --- | --- |
| Ph-CO-C6H3(NH-CO-CH3)(NH-C(SCH3)=N-COOCH3) | Toxascaris l. | 10 |
|  | Ascaris suum | 5 |
|  | Toxocara | 10 |
| Ph-CO-C6H3(NH-CO-CH2-CH2-CH3)(NH-C(SCH3)=N-COOCH3) | Ascaris suum | 5 |
|  | Toxocara | 5 |
|  | Toxascaris | 10 |
| Ph-CO-C6H3(NH-CO-C6H11)(NH-C(SCH3)=N-COOCH3) | Ascaris suum | 10 |
|  | Toxascaris | 5 |
| Ph-CO-C6H3(NH-CO-Ph)(NH-C(SCH3)=N-COOCH3) | Ascaris suum | 25 |
| Ph-CO-C6H3(NH-CO-CH2-CH3)(NH-C(SCH3)=N-COOCH3) | Ascaris suum | 5 |

Known preparation for comparison

| Benzimidazole-thiazole | Toxascaris l. | 5 × 50* |
| --- | --- | --- |
|  | Ascaris suum | 500 |

*Flucke, W. (1963) Die Kleintierpraxis 8, 176

EXAMPLE F

Heterakis spumosa/mice

Mice experimentally infected with *Heterakis spumosa* were treated at the end of the pre-patency time of the parasites.

The amount of active compound was administered orally as an aqueous suspension.

The degree of action of the preparation is determined by counting, after dissection, the worms remaining in the test animal in comparison to untreated control animals and calculating the percentage action therefrom.

The results are given in Table 6.

Table 6
(accompanying Example F)

| Active compound according to the invention | Minimum effective dose (red.>90%) in mg/kg |
|---|---|
| 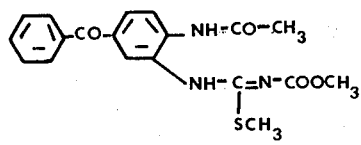 | 5 |
| 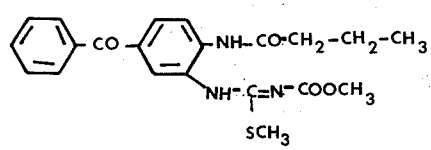 | 10 |
| 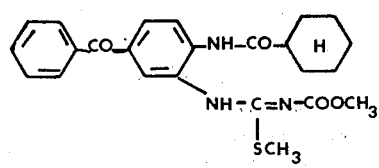 | 100 |
| 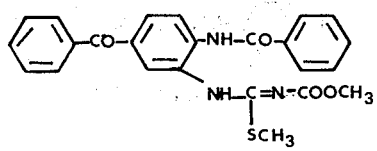 | 25 |
| 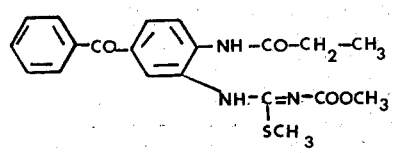 | 25 |

Table 6-continued
(accompanying Example F)

| Active compound according to the invention | Minimum effective dose (red.>90%) in mg/kg |
|---|---|
| Known preparation for comparison 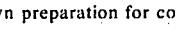 | 500 |

EXAMPLE G

Aspiculuris tetraptera/mice

Mice experimentally infected with *Aspiculuris tetraptera* were treated at the end of the pre-patency of the parasites.

The active compound was administered orally as an aqueous suspension.

The degree of reaction of the preparation is determined by counting, after dissection, the worms remaining in the test animal in comparison to untreated control animals and calculating the percentage action therefrom.

The results are given in Table 7.

Table 7
(accompanying Example G)

| Active compound according to the invention | Minimum effective dose (red. >90%) in mg/kg |
|---|---|
| 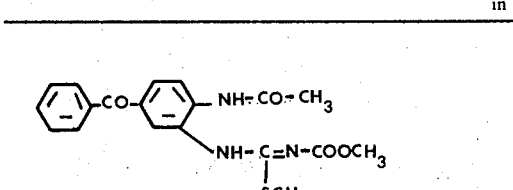 | 5 |
| 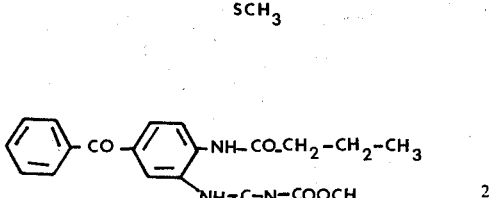 | 25 |
| 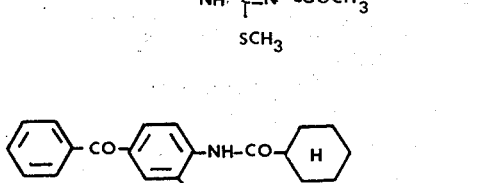 | 250 |
| 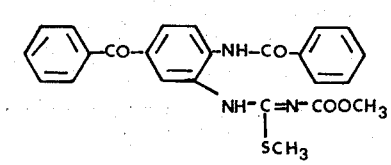 | 25 |

Table 7-continued
(accompanying Example G)

| Active compound according to the invention | Minimum effective dose (red. >90%) in mg/kg |
|---|---|
| [Structure: phenyl-CO-phenyl with NH-CO-CH₂-CH₃ and NH-C(SCH₃)=N-COOCH₃ substituents] | 10 |
| Known preparation for comparison | |
| [Structure: benzimidazole-thiazole] | 500 |

EXAMPLE H

Trichuris muris/mice

Mice experimentally infected with *Trichuris muris* were treated at the end of the pre-patency time of the parasites.

The amount of active compound was administered orally as an aqueous suspension.

The degree of action of the preparation is determined by counting, after dissection, the worms remaining in the test animal in comparison to untreated control animals and calculating the percentage action therefrom.

The results are given in Table 8.

Table 8
(accompanying Example H)

| Active compound according to the invention | Minimum effective dose (red. >90%) in mg/kg |
|---|---|
| [Structure: phenyl-CO-phenyl with NH-CO-CH₃ and NH-C(SCH₃)=N-COOCH₃] | 2.5 |
| [Structure: phenyl-CO-phenyl with NH-CO-CH₂-CH₂-CH₃ and NH-C(SCH₃)=N-COOCH₃] | 5 |

Table 8 -continued
(accompanying Example H)

| Active compound according to the invention | Minimum effective dose (red. >90%) in mg/kg |
|---|---|
| [Structure: phenyl-CO-phenyl with NH-CO-cyclohexyl and NH-C(SCH₃)=N-COOCH₃] | 250 |
| [Structure: phenyl-CO-phenyl with NH-CO-phenyl and NH-C(SCH₃)=N-COOCH₃] | 25 |
| [Structure: phenyl-CO-phenyl with NH-CO-CH₂-CH₃ and NH-C(SCH₃)=N-COOCH₃] | 10 |
| Known preparation for comparison | |
| [Structure: benzimidazole-thiazole] | inactive |

The following non-limitative examples more particularly point out and define the present invention:

EXAMPLE 1

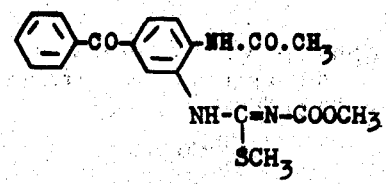

126 g (0.1 mol) of dimethyl sulphate are added dropwise at room temperature, while stirring, to 371 g (0.1 mol) of N-(2-acetamido-5-benzoylphenyl)-N'-methoxycarbonyl-thiourea of melting point 199°C and 4 g (0.1 mol) of NaOH in 300 ml of water, the mixture is subsequently stirred for a further 3 hours and N-(2-acetamido-5-benzoylphenyl)-N'-methoxycarbonyl-S-methylisothiourea is filtered off and recrystallized from ethanol; melting point 172°C with decomposition, yield 31 g.

The following compounds were produced in a manner analogous to that described above from the reactants set forth:

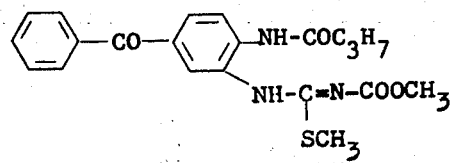

Melting point 158° with decomposition
from N-(2-butoxyamido-5-benzoylphenyl)-N'-methoxycarbonyl-thiourea

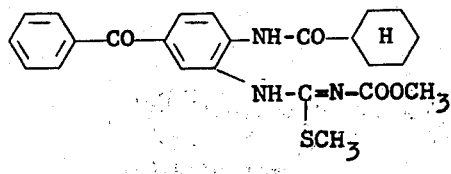

Melting point 140° with decomposition
from N-(2-cyclohexanecarbonamido-5-benzoylphenyl)-N'-methoxycarbonyl-thiourea

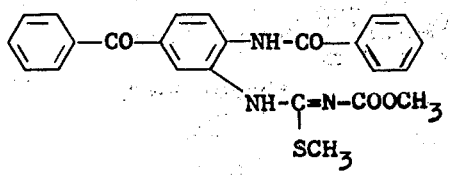

Melting point 139° with decomposition
from N-(2-benzamido-5-benzoylphenyl)-N'-methoxycarbonyl-thiourea

EXAMPLE 2

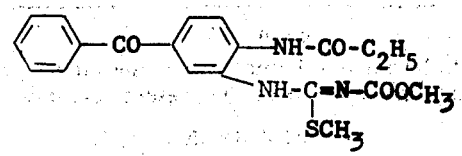

Melting point 168° with decomposition.
from N-(2-propionamido-5-benzoylphenyl)-N'-methoxycarbonyl-thiourea

EXAMPLE 3

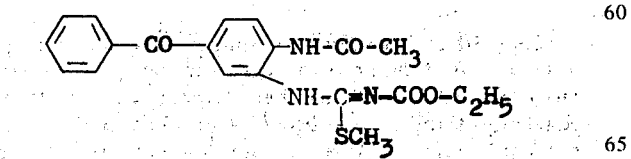

Melting point 205° with decomposition.

from N-(2-acetamido-5-benzoylphenyl)-N'-ethoxycarbonyl-thiourea

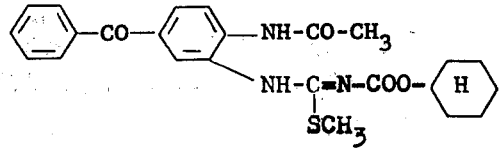

Melting point 195° with decomposition
from N-(2-acetamido-5-benzoylphenyl)-N'-cyclohexyloxycarbonyl-thiourea

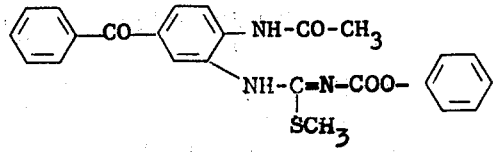

Melting point 152° with decomposition
from N-(2-acetamido-5-benzoylphenyl)-N'-phenoxycarbonyl-thiourea

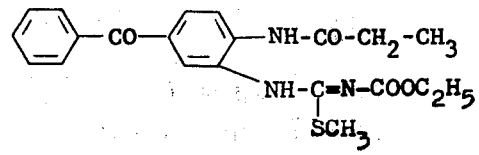

Melting point 168° with decomposition
from N-(2-propionamido-5-benzoylphenyl)-N'-ethoxycarbonyl-thiourea

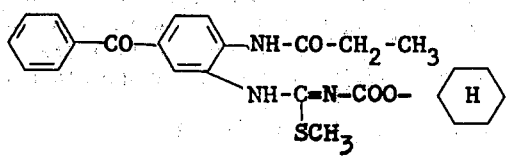

Melting point 170° with decomposition
from N-(2-propionamido-5-benzoylphenyl)-N'-cyclohexyloxycarbonyl-thiourea

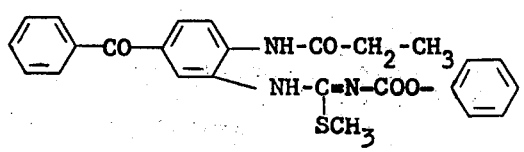

Melting point 154° with decomposition
from N-(2-propionamido-5-benzoylphenyl)-N'-phenoxycarbonyl-thiourea

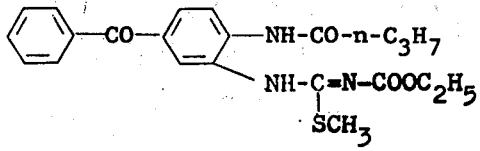

Melting point 155° with decomposition from N-(2-butyramido-5-benzoylphenyl)-N'-ethoxycarbonyl-thiourea

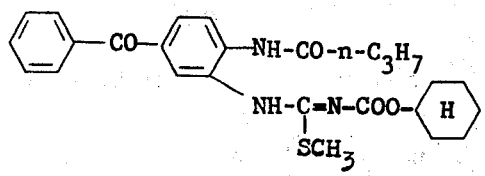

Melting point 151° with decomposition from N-(2-butyramido-5-benzoylphenyl)-N'-cyclohexyloxycarbonyl-thiourea

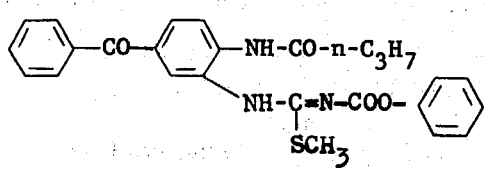

Melting point 142° with decomposition from N-(2-butyramido-5-benzoylphenyl)-N''-phenoxycarbonyl-thiourea The following non-limitative example illustrates the production of starting materials used in the process of the present invention:

EXAMPLE FOR PRODUCTION OF STARTING MATERIALS

N-(2-Acetamido-5-benzoylphenyl)-N'-methoxycarbonyl-thiourea, which was not per se known, can be obtained from 2-nitro-4-benzoylaniline in a three-stage process as follows:

1st stage:

Preparation of 2-nitro-4-benzoyl-acetanilide

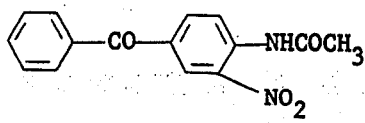

A solution of 26.1 g (0.33 mol) of acetyl chloride in 50 ml of dry benzene is added dropwise to a solution of 80.7 g (0.33 mol) of 2-nitro-4-benzoyl-aniline of melting point 143°C, which is known from the literature, and 26.4 g (0.33 mol) of pyridine in 800 ml of dry benzene while stirring at room temperature. When the slightly exothermic reaction has subsided the mixture is stirred for a further 1.5 hours at room temperature and a further 2 hours at 75°C. Thereafter the water-soluble pyridine hydrochloride which has separated out is filtered off hot and the 2-nitro-4-benzoylacetanilide which crystallizes out on cooling the filtrate is well stirred with dilute hydrochloric acid, filtered off, dried and purified by recrystallization from ethanol; melting point 145°C, yield 70 g. The yield can be further increased by working up the mother liquor by extracting it with dilute aqueous HCl, separating off and drying the organic phase, evaporating the solvent and recrystallizing the residue from ethanol.

2nd stage:

Preparation of 2-amino-4-benzoyl-acetanilide

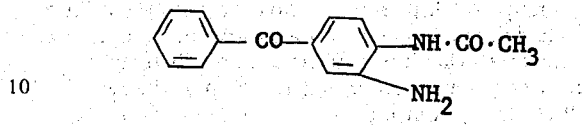

65 g of 2-nitro-4-benzoyl-acetanilide of melting point 145°C in 500 ml of tetrahydrofurane are hydrogenated with 5 g of Raney nickel at 50 atmosphere gauge pressure of hydrogen, allowing a reaction time of 3 hours. In the course thereof, the temperature rises from 20° to 35°C; the consumption of $H_2$ corresponds to the calculated amount. After cooling, the catalyst is filtered off, the solvent is evaporated and the only residue is recrystallized from ethanol. 2-Amino-4-benzoyl-acetanilide of melting point 136°C is thereby obtained in a yield of 38 g.

3rd stage:

Preparation of N-(2-acetamido-5-benzoylphenyl)-N'-methoxycarbonyl-thiourea

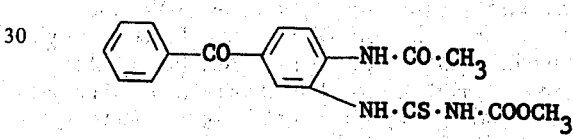

A solution prepared as follows is added dropwise to 127 g (0.5 mol) of 2-amino-4-benzoyl-acetanilide of melting point 136°C in 1,000 ml of acetone, while stirring at room temperature: 94.5 g (1 mol) of chloroformic acid methyl ester are added dropwise, while stirring and cooling with water, to 97.2 g (1 mol) of potassium thiocyanate in 365 ml of dry acetone. (This assumes 50% reaction). Towards the end of the dropwise addition the temperature is allowed to rise to 40°C and the mixture is stirred for a further hour at this temperature and then filtered. After completion of the introduction of this solution, the mixture is stirred for a further hour at room temperature and for 4 hours at 60°C. It is then cooled to 10°C and the N-(2-acetamido-5-benzoylphenyl)-N'-methoxycarbonyl-thiourea which crystalizes out is rinsed with a little acetone and dried; melting point 199°C, yield 153 g.

The remaining N-(2-acylamido-5-benzoylphenyl)-N'-alkoxycarbonyl-thioureas of the formula (II) employed in the process of the present invention can be prepared analogously.

What is claimed is:
1. A benzoylphenylisothiourea of the formula:

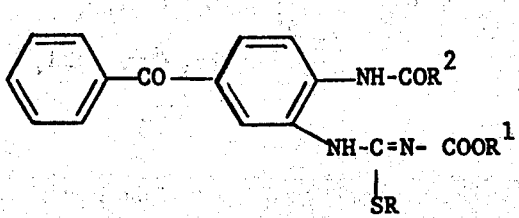

wherein R is alkyl of 1 to 4 carbon atoms, alkenyl of 2 to 4 carbon atoms, cycloalkyl of 5 to 6 carbon atoms or benzyl;

R¹ is alkyl of 1 to 4 carbon atoms, cyclohexyl or phenyl; and

R² is lower alkyl, cycloalkyl of 5 or 6 carbon atoms, phenyl, tolyl, phenoxymethyl, benzyl, mono-lower alkylamino, cyano lower alkylamino, lower alkoxy lower alkylamino, benzylamino or phenylamino.

2. A compound according to claim 1 wherein R is methyl, ethyl, isopropyl, allyl, cyclohexyl or benzyl;

R¹ is methyl, ethyl, isopropyl, or sec.-butyl; and

R² is methyl, ethyl, n-propyl, isopropyl, n-butyl, isobutyl, isoamyl, cyclopentyl, cyclohexyl, benzyl, phenoxymethyl, phenyl, tolyl, methylamino, propylamino, butylamino, cyanopentylamino, methoxyethylamino, ethoxypropylamino, benzylamino or phenylamino.

3. A compound according to claim 1 wherein R is alkyl of 1 to 4 carbon atoms, alkenyl of 2 to 4 carbon atoms, or cyclohexyl;

R¹ is alkyl of 1 to 4 carbon atoms; and

R² is lower alkyl, cycloalkyl of 5 or 6 carbon atoms, phenyl, phenoxymethyl, benzyl, mono-lower alkylamino, cyano lower alkylamino, lower alkoxy lower alkylamino, benzylamino or phenylamino.

4. A compound according to claim 1 wherein
R is methyl, ethyl, isopropyl, allyl or cyclohexyl;
R¹ is methyl, ethyl, isopropyl or sec.-butyl; and
R² is methyl, ethyl, propyl, isopropyl, butyl, isobutyl, amyl, isoamyl, cyclopentyl, cyclohexyl, phenyl, phenoxymethyl, benzyl, methylamino, ethylamino, butylamino, cyano pentylamino, methoxyethylamino, benzylamino or phenylamino.

5. A compound according to claim 1 wherein
R is alkyl of 1 or 2 carbon atoms;
R¹ is alkyl of 1 or 2 carbon atoms, cyclohexyl or phenyl; and
R² is alkyl of 1 to 4 carbon atoms, cyclohexyl or phenyl.

6. A compound according to claim 1 wherein
R is methyl;
R¹ is methyl, ethyl, cyclohexyl, or phenyl; and
R² is methyl, ethyl, propyl, cyclohexyl or phenyl.

7. The compound according to claim 1 which is

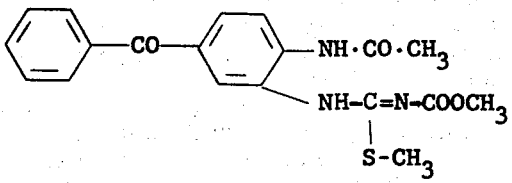

8. The compound according to claim 1 which is

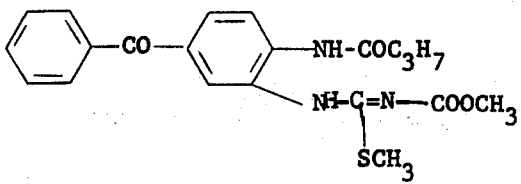

9. The compound according to claim 1 which is

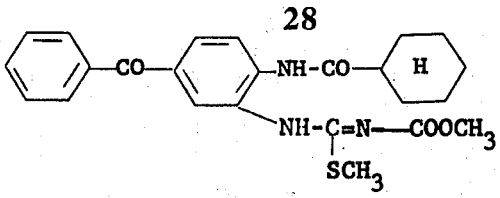

10. The compound according to claim 1 which is

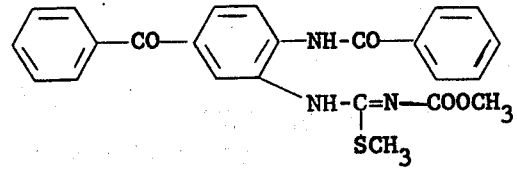

11. The compound according to claim 1 which is

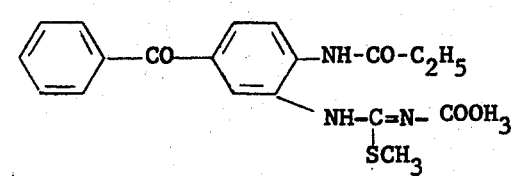

12. The compound according to claim 1 which is

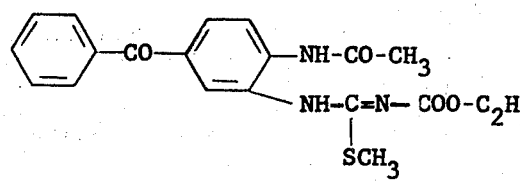

13. The compound according to claim 1 which is

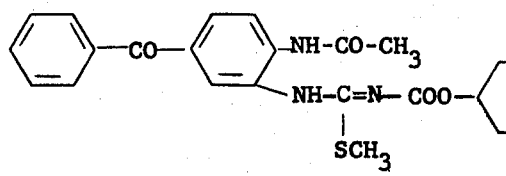

14. The compound according to claim 1 which is

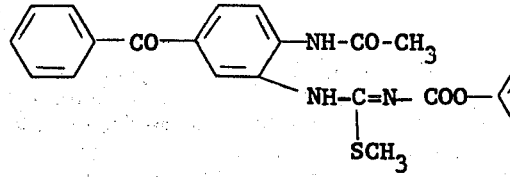

15. The compound according to claim 1 which is

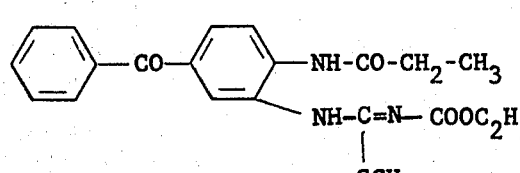

16. The compound according to claim 1 which is

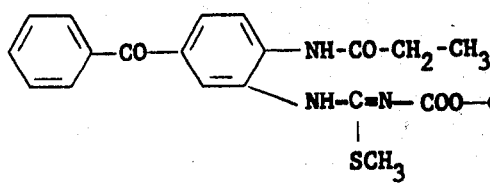
17. The compound according to claim 1 which is
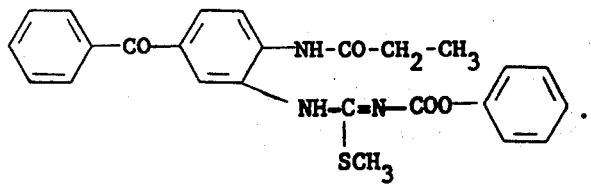
18. The compound according to claim 1 which is
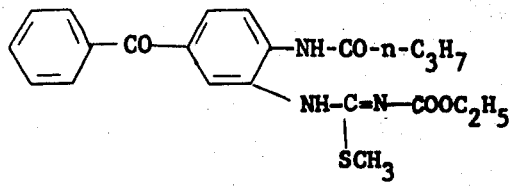
19. The compound according to claim 1 which is
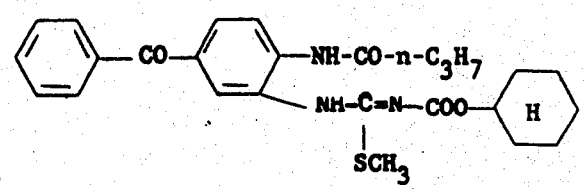
20. The compound according to claim 1 which is
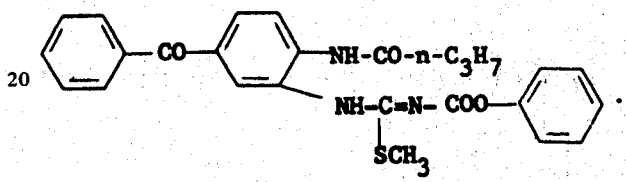
* * * * *